US009510865B2

(12) United States Patent
Elsebaie et al.

(10) Patent No.: US 9,510,865 B2
(45) Date of Patent: Dec. 6, 2016

(54) GROWTH DIRECTED VERTEBRAL FIXATION SYSTEM WITH DISTRACTIBLE CONNECTOR(S) AND APICAL CONTROL

(71) Applicant: K2M, Inc., Leesburg, VA (US)

(72) Inventors: Hazem Elsebaie, Giza (EG); Behrooz Akbarnia, La Jolla, CA (US)

(73) Assignee: K2M, Inc., Leesburg, VA (US)

( * ) Notice: Subject to any disclaimer, the term of this patent is extended or adjusted under 35 U.S.C. 154(b) by 74 days.

(21) Appl. No.: 14/480,047

(22) Filed: Sep. 8, 2014

(65) Prior Publication Data

US 2014/0379033 A1    Dec. 25, 2014

Related U.S. Application Data

(60) Division of application No. 12/873,582, filed on Sep. 1, 2010, now Pat. No. 8,828,058, which is a continuation-in-part of application No. PCT/US2009/063833, filed on Nov. 10, 2009.

(30) Foreign Application Priority Data

Nov. 11, 2008    (EG) ................. 2008111840

(51) Int. Cl.
    *A61B 17/70*    (2006.01)
(52) U.S. Cl.
    CPC ....... *A61B 17/7014* (2013.01); *A61B 17/7001* (2013.01); *A61B 17/701* (2013.01);
    (Continued)

(58) Field of Classification Search
    CPC ................................................ A61B 17/7053
    See application file for complete search history.

(56) References Cited

U.S. PATENT DOCUMENTS 2,774,350 A    12/1956  Cleveland, Jr.
3,242,922 A     3/1966  Thomas
(Continued)

FOREIGN PATENT DOCUMENTS

DE    2644735 A1    4/1977
DE    2845647 A1    5/1980
(Continued)

OTHER PUBLICATIONS

Machine English translation of Fortin et al WO 2006/010844, Jan. 8, 2016.*

(Continued)

*Primary Examiner* — Jan Christopher Merene
(74) *Attorney, Agent, or Firm* — Carter, DeLuca, Farrell & Schmidt, LLP

(57) ABSTRACT

Growth directed correction of a spine via apical vertebral control includes securing a correction system to a first vertebra and a second vertebra of the spine, the correction system defining a correction axis extending between the first and second vertebra and securing the correction system to a third vertebra intermediate the first and second vertebra, the correction system securing the third vertebra at a fixed distance from the correction axis. The correction system is secured to the first and second vertebra such that the first and second vertebra are able to grow away from one another in a direction substantially parallel to the correction axis.

5 Claims, 6 Drawing Sheets

(52) U.S. Cl.
CPC ........ *A61B 17/705* (2013.01); *A61B 17/7025* (2013.01); *A61B 17/7041* (2013.01); *A61B 17/7053* (2013.01)

(56) References Cited

U.S. PATENT DOCUMENTS

| | | |
|---|---|---|
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A | 3/1978 | Nissinen |
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,634,445 A | 1/1987 | Helal |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,473 A | 7/1994 | Howland |
| 5,330,474 A | 7/1994 | Lin |
| 5,352,226 A | 10/1994 | Lin |
| 5,360,431 A | 11/1994 | Puno et al. |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,466,238 A | 11/1995 | Lin |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,527,314 A | 6/1996 | Brumfield et al. |
| 5,534,002 A | 7/1996 | Brumfield et al. |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,601,554 A | 2/1997 | Howland et al. |
| 5,609,592 A | 3/1997 | Brumfield et al. |
| 5,611,800 A | 3/1997 | Davis et al. |
| 5,620,443 A | 4/1997 | Gertzbein et al. |
| 5,630,816 A | 5/1997 | Kambin |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A | 9/1997 | Martin |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,716,355 A | 2/1998 | Jackson et al. |
| 5,720,746 A | 2/1998 | Soubeiran |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,885,285 A | 3/1999 | Simonson |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A | 8/1999 | Petreto |
| 5,947,967 A | 9/1999 | Barker |
| 5,964,769 A | 10/1999 | Wagner et al. |
| 5,976,135 A | 11/1999 | Sherman et al. |
| 5,980,521 A | 11/1999 | Montague et al. |
| 5,984,924 A | 11/1999 | Asher et al. |
| 5,989,256 A | 11/1999 | Kuslich et al. |
| 6,015,409 A | 1/2000 | Jackson |
| 6,033,412 A | 3/2000 | Losken et al. |
| 6,039,738 A | 3/2000 | Sanders et al. |
| 6,053,921 A | 4/2000 | Wagner et al. |

(56) References Cited

U.S. PATENT DOCUMENTS

| | | |
|---|---|---|
| 6,066,140 A | 5/2000 | Gertzbein et al. |
| 6,077,268 A | 6/2000 | Farris et al. |
| 6,080,156 A | 6/2000 | Asher et al. |
| 6,083,224 A | 7/2000 | Gertzbein et al. |
| 6,086,590 A | 7/2000 | Margulies et al. |
| 6,101,678 A | 8/2000 | Malloy et al. |
| 6,110,173 A | 8/2000 | Thomas, Jr. |
| 6,123,706 A | 9/2000 | Lange |
| 6,132,431 A | 10/2000 | Nilsson et al. |
| 6,132,464 A | 10/2000 | Martin |
| 6,136,000 A | 10/2000 | Louis et al. |
| 6,176,861 B1 | 1/2001 | Bernstein et al. |
| 6,231,575 B1 | 5/2001 | Krag |
| 6,248,106 B1 | 6/2001 | Ferree |
| 6,251,111 B1 | 6/2001 | Barker et al. |
| 6,254,603 B1 | 7/2001 | Gertzbein et al. |
| 6,261,288 B1 | 7/2001 | Jackson |
| 6,273,914 B1 | 8/2001 | Papas |
| 6,277,120 B1 | 8/2001 | Lawson |
| 6,283,967 B1 | 9/2001 | Troxell et al. |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,391,030 B1 | 5/2002 | Wagner et al. |
| 6,402,749 B1 | 6/2002 | Ashman |
| 6,402,752 B2 | 6/2002 | Schäffler-Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,471,704 B2 | 10/2002 | Gertzbein et al. |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,565,605 B2 | 5/2003 | Goble et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,585,738 B1 | 7/2003 | Mangione et al. |
| 6,589,243 B1 | 7/2003 | Viart et al. |
| 6,602,254 B2 | 8/2003 | Gertzbein et al. |
| 6,602,818 B2 | 8/2003 | Choi, II et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,641,585 B2 | 11/2003 | Sato et al. |
| 6,645,207 B2 | 11/2003 | Dixon et al. |
| 6,651,320 B1 | 11/2003 | Yagi et al. |
| 6,656,185 B2 | 12/2003 | Gleason et al. |
| 6,669,729 B2 | 12/2003 | Chin |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |
| 6,709,435 B2 | 3/2004 | Lin |
| 6,736,817 B2 | 5/2004 | Troxell et al. |
| 6,749,612 B1 | 6/2004 | Conchy et al. |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,811,567 B2 | 11/2004 | Reiley |
| 6,835,207 B2 | 12/2004 | Zacouto et al. |
| 6,840,127 B2 | 1/2005 | Moran |
| 6,860,884 B2 | 3/2005 | Shirado et al. |
| 6,887,241 B1 | 5/2005 | McBride et al. |
| 6,902,580 B2 | 6/2005 | Fallin et al. |
| 6,946,000 B2 | 9/2005 | Senegas et al. |
| 6,966,910 B2 | 11/2005 | Ritland |
| 6,966,930 B2 | 11/2005 | Arnin et al. |
| 6,974,478 B2 | 12/2005 | Reiley et al. |
| 6,986,771 B2 | 1/2006 | Paul et al. |
| 7,008,423 B2 | 3/2006 | Assaker et al. |
| 7,018,379 B2 | 3/2006 | Drewry et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,051,451 B2 | 5/2006 | Augostino et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,090,698 B2 | 8/2006 | Goble et al. |
| 7,104,992 B2 | 9/2006 | Bailey |
| RE39,325 E | 10/2006 | Bryan |
| 7,128,743 B2 | 10/2006 | Metz-Stavenhagen |
| 7,137,986 B2 | 11/2006 | Troxell et al. |
| 7,160,312 B2 | 1/2007 | Saadat |
| 7,220,262 B1 | 5/2007 | Hynes |
| 7,261,714 B2 | 8/2007 | Richelsoph |
| 7,270,665 B2 | 9/2007 | Morrison et al. |
| 7,290,347 B2 | 11/2007 | Augostino et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,406,775 B2 | 8/2008 | Funk et al. |
| 7,445,635 B2 | 11/2008 | Fallin et al. |
| 7,473,267 B2 | 1/2009 | Nguyen et al. |
| 7,473,269 B1 | 1/2009 | Hynes |
| 7,481,828 B2 | 1/2009 | Mazda et al. |
| 7,507,242 B2 | 3/2009 | Triplett et al. |
| 7,524,324 B2 | 4/2009 | Winslow et al. |
| 7,566,345 B2 | 7/2009 | Fallin et al. |
| 7,588,578 B2 | 9/2009 | Triplett et al. |
| 7,588,590 B2 | 9/2009 | Chervitz et al. |
| 7,591,836 B2 | 9/2009 | Dick et al. |
| 7,594,924 B2 | 9/2009 | Albert et al. |
| 7,611,526 B2 | 11/2009 | Carl et al. |
| 7,618,453 B2 | 11/2009 | Goble et al. |
| 7,618,455 B2 | 11/2009 | Goble et al. |
| 7,621,955 B2 | 11/2009 | Goble et al. |
| 7,648,521 B2 | 1/2010 | Hestad |
| 7,658,753 B2 | 2/2010 | Carl et al. |
| 7,674,293 B2 | 3/2010 | Kuiper et al. |
| 7,678,136 B2 | 3/2010 | Doubler et al. |
| 7,691,145 B2 | 4/2010 | Reiley et al. |
| 7,708,762 B2 | 5/2010 | McCarthy et al. |
| 7,717,940 B2 | 5/2010 | Woods et al. |
| 7,717,942 B2 | 5/2010 | Schumacher |
| 7,722,647 B1 | 5/2010 | Wang et al. |
| 7,722,648 B2 | 5/2010 | Drewry et al. |
| 7,753,937 B2 | 7/2010 | Chervitz et al. |
| 7,758,581 B2 | 7/2010 | Chervitz et al. |
| 7,771,474 B2 | 8/2010 | Cordaro |
| 7,794,476 B2 | 9/2010 | Wisnewski |
| 7,794,478 B2 | 9/2010 | Nilsson |
| 7,799,054 B2 | 9/2010 | Kwak et al. |
| 7,819,902 B2 | 10/2010 | Abdelgany et al. |
| 7,833,252 B2 | 11/2010 | Justis et al. |
| 7,837,714 B2 | 11/2010 | Drewry et al. |
| 7,842,071 B2 | 11/2010 | Hawkes |
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |

(56) References Cited

U.S. PATENT DOCUMENTS

| | | |
|---|---|---|
| 7,959,653 B2 | 6/2011 | Thramann et al. |
| 7,963,978 B2 | 6/2011 | Winslow et al. |
| 7,985,243 B2 | 7/2011 | Winslow et al. |
| 8,012,184 B2 | 9/2011 | Schlapfer et al. |
| 8,016,860 B2 | 9/2011 | Carl et al. |
| 8,021,400 B2 | 9/2011 | Marino et al. |
| 8,029,543 B2 | 10/2011 | Young et al. |
| 8,029,546 B2 | 10/2011 | Capote et al. |
| 8,034,078 B2 | 10/2011 | Laskowitz et al. |
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |
| 8,057,472 B2 | 11/2011 | Walker et al. |
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,147,524 B2 | 4/2012 | Piza Vallespir |
| 8,162,979 B2 | 4/2012 | Sachs et al. |
| 8,167,908 B2 | 5/2012 | Ely et al. |
| 8,192,471 B2 | 6/2012 | Ludwig et al. |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,518,086 B2 | 8/2013 | Seme et al. |
| 8,828,058 B2 | 9/2014 | Elsebaie et al. |
| 2001/0037111 A1 | 11/2001 | Dixon et al. |
| 2002/0032442 A1 | 3/2002 | Altarac et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0045878 A1 | 3/2003 | Petit et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz-Stavenhagen |
| 2006/0085075 A1 | 4/2006 | McLeer |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |
| 2007/0005062 A1 | 1/2007 | Lange et al. |
| 2007/0016296 A1 | 1/2007 | Triplett et al. |
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0161987 A1 | 7/2007 | Capote et al. |
| 2007/0161993 A1 | 7/2007 | Lowery et al. |
| 2007/0161994 A1 | 7/2007 | Lowery et al. |
| 2007/0162002 A1 | 7/2007 | Tornier |
| 2007/0167946 A1 | 7/2007 | Triplett et al. |
| 2007/0167947 A1 | 7/2007 | Gittings |
| 2007/0168035 A1 | 7/2007 | Koske |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |

(56) References Cited

U.S. PATENT DOCUMENTS

| | | |
|---|---|---|
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270803 A1 | 11/2007 | Giger et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276374 A1 | 11/2007 | Broman et al. |
| 2007/0288011 A1 | 12/2007 | Logan |
| 2007/0288024 A1 | 12/2007 | Gollogly |
| 2008/0015577 A1 | 1/2008 | Loeb |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0045954 A1 | 2/2008 | Reiley et al. |
| 2008/0065069 A1 | 3/2008 | Betz et al. |
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0132951 A1 | 6/2008 | Reiley et al. |
| 2008/0140202 A1 | 6/2008 | Allard et al. |
| 2008/0167688 A1 | 7/2008 | Fauth et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0306535 A1 | 12/2008 | Winslow et al. |
| 2008/0306536 A1 | 12/2008 | Frigg et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1 | 1/2009 | Sachs et al. |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0194206 A1 | 8/2009 | Jeon et al. |
| 2009/0204156 A1 | 8/2009 | McClintock et al. |
| 2009/0259256 A1 | 10/2009 | Miller |
| 2009/0281575 A1 | 11/2009 | Carls et al. |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0106192 A1 | 4/2010 | Barry |
| 2010/0137913 A1 | 6/2010 | Khatchadourian et al. |
| 2010/0249836 A1 | 9/2010 | Seme |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0318129 A1 | 12/2010 | Seme et al. |
| 2011/0054536 A1 | 3/2011 | Elsebaie et al. |
| 2011/0060367 A1 | 3/2011 | Stauber |
| 2011/0066188 A1 | 3/2011 | Seme et al. |
| 2011/0245876 A1 | 10/2011 | Brumfield |
| 2012/0109197 A1 | 5/2012 | Carl et al. |
| 2012/0203282 A1 | 8/2012 | Sachs et al. |
| 2012/0221057 A1 | 8/2012 | Zhang et al. |
| 2013/0123851 A1 | 5/2013 | Seme et al. |
| 2013/0123853 A1 | 5/2013 | Seme et al. |
| 2013/0184757 A1 | 7/2013 | Seme et al. |
| 2013/0211455 A1 | 8/2013 | Seme |
| 2013/0231703 A1 | 9/2013 | Seme et al. |
| 2014/0236234 A1 | 8/2014 | Kroll et al. |

FOREIGN PATENT DOCUMENTS

| | | |
|---|---|---|
| EP | 0418387 A1 | 3/1991 |
| EP | 0260044 B1 | 5/1991 |
| EP | 0322334 B1 | 2/1992 |
| EP | 1281361 A1 | 2/2003 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| FR | 2900563 A1 | 11/2007 |
| GB | 0780652 A | 8/1957 |
| JP | 2010528779 A | 8/2010 |
| SU | 0888968 A1 | 12/1981 |
| WO | WO9213496 A1 | 8/1992 |
| WO | WO2004017705 A2 | 3/2004 |
| WO | WO2006010844 A1 | 2/2006 |
| WO | WO2006017641 A2 | 2/2006 |
| WO | WO2006136937 A2 | 12/2006 |
| WO | WO2007051924 A1 | 5/2007 |
| WO | WO2008086467 A2 | 7/2008 |
| WO | WO2008154313 A1 | 12/2008 |
| WO | 2010030906 A1 | 3/2010 |
| WO | WO2010053662 A1 | 5/2010 |
| WO | WO2010056650 A1 | 5/2010 |
| WO | WO2010111500 A2 | 9/2010 |
| WO | WO2014172632 A2 | 10/2014 |

OTHER PUBLICATIONS

Berry, James L. et al., A Morphometric Study of Human Lumbar and Selected Thoracic Vertebrae, 12 SPINE 362 (1987).

(56) References Cited

OTHER PUBLICATIONS

Eglin, D. et al., "Degradable Polymeric Materials for Osteosynthesis: tutorial", European Cells and Materials, vol. 16, 2008, pp. 80-91.
European Search Report issued in EP Application No. 12154799, completed Mar. 2, 2012, 9 pages.
Fujita, Masaru et al., A Biomechanical Analysis of Sublaminar and Subtransverse Process Fixation Using Metal Wires and Polyethylene Cables, 31 SPINE 2202 (2006).
Girardi, Federico P. et al., Safety of Sublaminar Wires With Isola Instrumentation for the Treatment of Idiopathic Scoliosis, 25 SPINE 691 (2000).
International Application No. PCT/US2008/065979, filed Jun. 5, 2008, entitled Medical Device and Method to Correct Deformity.
International Application No. PCT/US2009/063833, filed Nov. 10, 2009, entitled Growth Directed Vertebral Fixation System With Distractible Connector(s) and Apical Control.
International Application No. PCT/US2010/028684, filed Mar. 25, 2010, entitled Semi-Constrained Anchoring System.
International Search Report and Written Opinion issued in PCT/US2005/027692, mailed May 19, 2008, 4 pages.
International Search Report and Written Opinion issued in PCT/US2008/065979, mailed Oct. 2, 2008, 7 pages.
International Search Report and Written Opinion issued in PCT/US2009/063833, mailed Mar. 15, 2010, 14 pages.
International Search Report and Written Opinion issued in PCT/US2010/028684, mailed Sep. 28, 2010, 19 pages.
International Search Report and Written Opinion issued in PCT/US2010/036375, mailed Sep. 10, 2010, 16 pages.
International Search Report and Written Opinion issued in PCT/US2010/047117, mailed Dec. 2, 2010.
International Search Report and Written Opinion issued in PCT/US2011/049693, mailed Nov. 15, 2011, 16 pages.
International Search Report and Written Opinion issued in PCT/US2012/040493, mailed Aug. 21, 2012, 15 pages.
International Search Report and Written Opinion issued in PCT/US2012/065262, mailed Feb. 5, 2013, 8 pages.
International Search Report and Written Opinion issued in PCT/US2013/065488, mailed Feb. 18, 2014, 10 pages.
Invitation to Pay Additional Fees and Partial Search Report issued in PCT/US2010/028684, mailed Jun. 30, 2010, 6 pages.
Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).
Molnar, Szabolcs et al., Ex Vivo and In Vitro Determination of the Axial Rotational Axis of the Human Thoracic Spine, 31 SPINE E984 (2006).
Rajasekaran, S. et al., Eighteen-Level Analysis of Vertebral Rotation Following Harrington-Luque Instrumentation in Idiopathic Scoliosis, 76 J Bone Joint Surg Am. 104 (1994).
U.S. Appl. No. 12/411,558, filed Mar. 26, 2009, entitled Alignment System With Longitudinal Support Features.
U.S. Appl. No. 12/411,562, filed Mar. 26, 2009, entitled Semi-Constrained Anchoring System.
U.S. Appl. No. 12/485,796, filed Jun. 16, 2009 entitled Deformity Alignment System With Reactive Force Balancing.
U.S. Appl. No. 12/560,199, filed Sep. 15, 2009, entitled Growth Modulation System.
Wenger, Dennis R. et al., Biomechanics of Scoliosis Correction by Segmental Spinal Instrumentation, 7 SPINE 260 (1982).
White III, Augustus A. et al., Biomechancis of the Spine 28-29, Tbl. 1-5 (2d ed. 1990).
Australian Office Action dated Apr. 11, 2016, issued in Australian Application No. 2015201395.
Japanese Office Action dated Feb. 23, 2016, issued in Japanese Application No. 2013-527184.
Japanese Office Action dated May 14, 2015, issued in Japanese Application No. 2013-527184.
Chinese Office Action dated Sep. 6, 2015, issued in Chinese Application No. 2011800424658.

\* cited by examiner

GROWTH DIRECTED VERTEBRAL FIXATION SYSTEM WITH DISTRACTIBLE CONNECTOR(S) AND APICAL CONTROL

CROSS-REFERENCE

This application is a divisional application of U.S. application Ser. No. 12/873,582, filed Sep. 1, 2010, and entitled "Growth Directed Vertebral Fixation System with Distractible Connector(s) and Apical Control," now U.S. Pat. No. 8,828,058, which is a continuation-in-part under 35 U.S.C. §120 of international application number PCT/US2009/063833, filed Nov. 10, 2009, and entitled "Growth Directed Vertebral Fixation System with Distractible Connector(s) and Apical Control," which claims priority to Egyptian Patent Application No. 2008111840 (alternatively referenced as 1840/2008), filed on Nov. 11, 2008, entitled "Self Expandable Vertebral Instrumentation System with Apical Deformity Control," which is incorporated herein by reference in its entirety.

BACKGROUND

Early onset scoliosis and scoliosis in the growing spine poses a great challenge in their treatment. In progressive cases, the spine cannot usually be controlled by bracing or even casting and it will grow accentuating the deformity with all its known consequences. On the other hand, correction, fixation, and fusion of the spine will prevent further growth of the fused spine with serious effects on the development of the cardiovascular and pulmonary system, physical appearance, and psychological impacts.

Early onset scoliosis has more recently been treated surgically either by serial distractions or growth directed mechanisms. Serial distractions using "growing rod" systems have been more reliable and have achieved a more predictable outcome. These "growing rod" systems use tandem or domino connectors designed to allow periodic distractions (e.g., every few months) via surgical approach under anesthesia. Growth directed mechanisms have been used in "Luque Trolley" techniques applying segmental wires attached to the vertebrae and rods longer than the instrumented segment to allow for directed growth of the spine by forcing the spine to follow the rods. Some recent trials have used pedicle screws instead of wires—again allowing the heads of the screws attached to the vertebrae to slide along the longer rods with growth.

Both the "growing rod" and the "growth directed" mechanisms, in current systems, are far from being fully satisfactory in the treatment of early onset scoliosis. For example, the "growing rods" have to be distracted surgically every few months for many years with all the disadvantages of multiple surgeries and anesthetic administration in the pediatric age group. In addition to the problems arising from skin and soft tissue opening, the frequent force applied to distract these systems can cause implant failures in addition to the potential negative effects of forceful spinal cord distractions.

The "growth directed" and Luque Trolley type of segmental instrumentations do not require frequent distractions. These systems, however, have not been satisfactory, mainly due to their inability to control rotation, the loss of correction, and spontaneous fusion, which have led to their failure. Even after trials to replace the wires with pedicle screws, there are still many potential problems, including auto fusion after segmental exposure to insert the pedicle screws and a high possibility of jamming between the screw rod junctions preventing smooth gliding of the screws on the rod. Another problem includes the increased risk, time consumption, and radiation exposure needed to insert the large number of multilevel pedicle screws in this very young age group. Furthermore, in these systems, the amount of growth possible before another surgery is limited to the parts of the rod left protruding from the top and bottom screws.

SUMMARY

The present invention, according to some embodiments, relates to a system designed to avoid the disadvantages of the prior art and to make the best use of the power of the growth of the spine by controlling and redirecting spinal growth as well as deforming forces of the spine to allow for longitudinal growth and to correct the residual deformity. Attaching vertebral fixation points proximal and distal to the deformed area of the spine, while strongly fixing the apex of the curve, allows this system to have the maximum control of the curve, while allowing all the vertebrae included in the curve above and below the apex to grow freely. This growth is permitted and directed by one or more connectors which are inserted between these fixation points by sliding of the rods attached to the fixation points within the connectors. Apical control should be strong and reliable to counteract the main deforming forces at the apex, thereby preventing its rotation and angulation. In some embodiments, the main correction of the curve occurs at the time of insertion of the system. Then, with time and growth, the system will allow for longitudinal growth of the spine with additional correction of the curve. As the distance between the rod and the apex of the deformity is fixed, any increase in the distance between the proximal and distal fixation points of the system will lead to a proportional decrease in the scoliosis angle.

Some embodiments address a vertebral fixation system to be used in spinal deformities in the growing spine for the pediatric and adolescent age groups. In some embodiments, the system corrects the scoliosis and allows spinal growth without frequent surgeries or complex technology by directing and controlling the forces that otherwise cause the spine to deform while growing. The system is inserted, or implanted, and includes proximal, distal, and apical vertebral fixation with the use of distractible connectors between the proximal and apical vertebrae and the distal and apical vertebrae.

After insertion, the connectors, or connector assembly, of the system permit the rod, which is fixed to the vertebrae at both ends of the curve, to slide inside one or more cylindrical members to allow for spinal growth. Meanwhile, apical vertebral fixation to the system prevents the spine from rotation or angulation, thereby preventing further deformity and even inducing more correction with time. In some embodiments, the growth directed corrective process will continue until the rod(s)/connector(s) sliding limit is exhausted (e.g., after many years).

This summary is not meant to be limiting in nature. While multiple embodiments are disclosed herein, still other embodiments of the present invention will become apparent to those skilled in the art from the following detailed description, which shows and describes illustrative embodiments of the invention. Accordingly, the drawings and detailed description are to be regarded as illustrative in nature and not restrictive.

As previously indicated, this description of the drawings is not meant to be limiting in nature.

DETAILED DESCRIPTION

Figure 1:
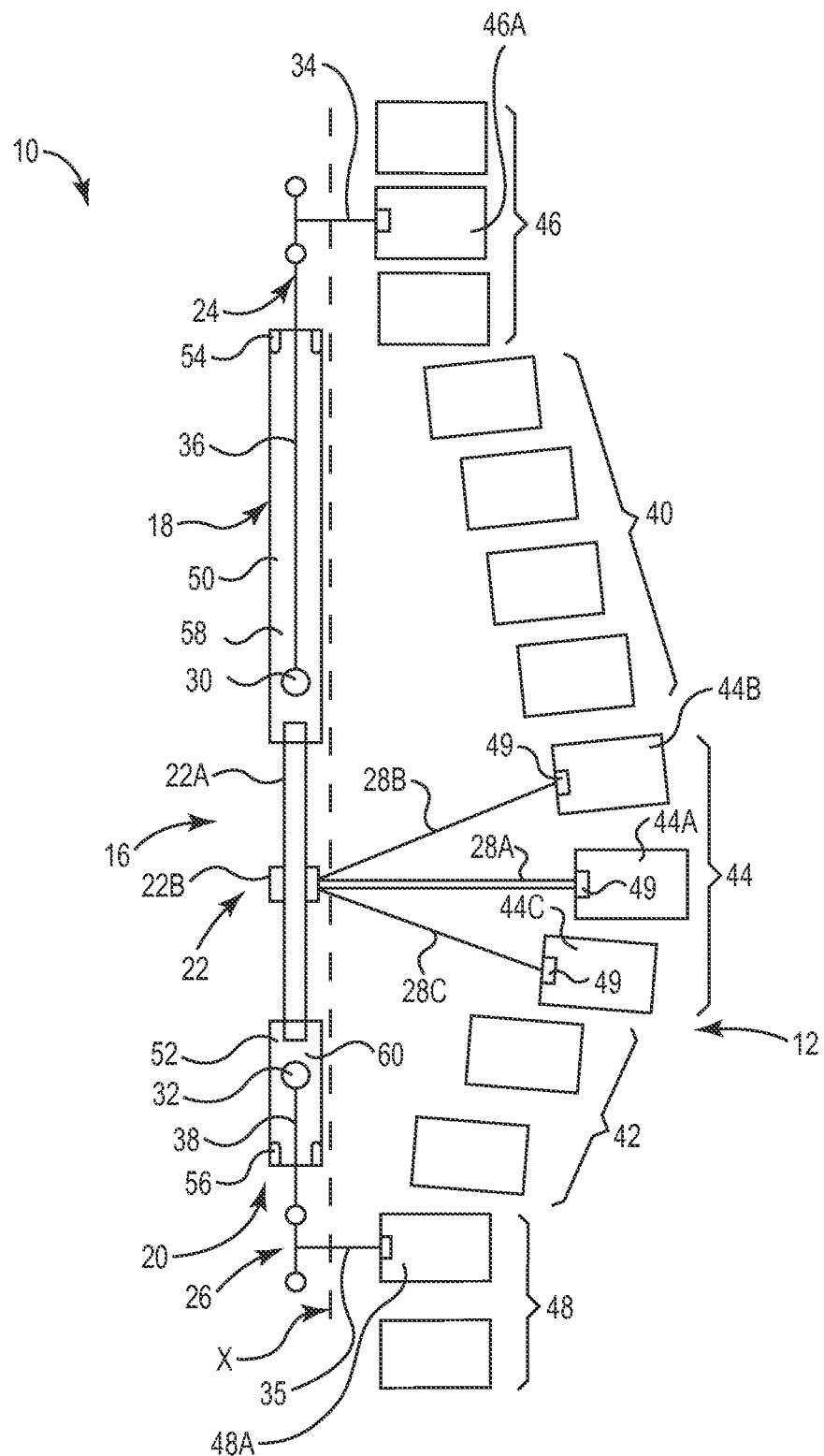
FIG. 1 is a schematic view of a corrective system secured along a spine tending to exhibit a defective curvature with a concave aspect, according to some embodiments.
Figure 2:
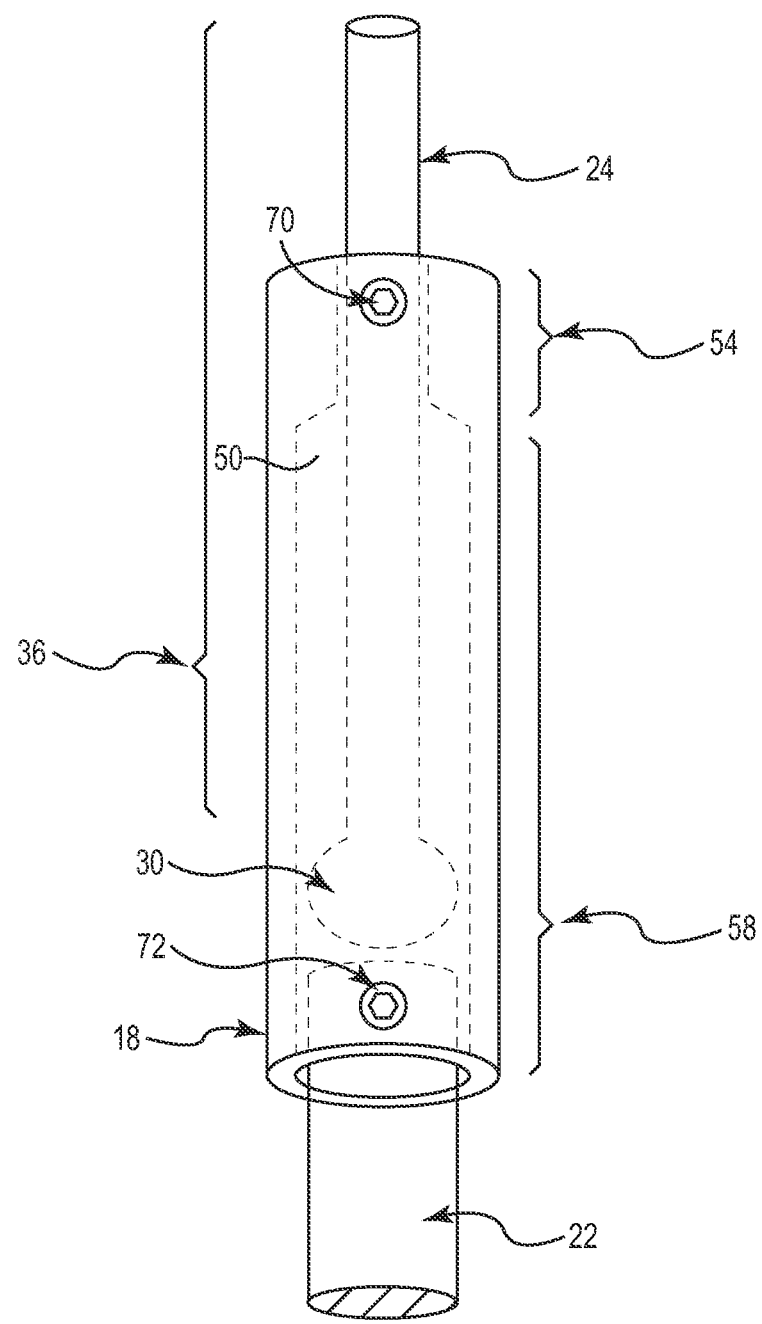
FIG. 2 shows a first connector and portions of a first rod and a middle assembling segment of the system of FIG. 1, according to some embodiments.

FIG. 1 is a schematic view of a system 10 for growth directed correction of a spine 12 via control of one or more apical vertebrae. The system 10 is secured to a spine 12 along a concave aspect of its defective curvature. In some embodiments, the system 10 includes a hosting connector assembly 16 including a first connector 18, a second connector 20, and a middle assembling segment 22. In the various embodiments, the system 10 further includes a first rod 24, a second rod 26, and an intermediate connector assembly 28. FIG. 2 shows the first connector 18 and portions of the first rod 24 and the middle assembling segment 22.

The first and second rods 24, 26 are adapted to extend along the spine 12 and optionally differ in length as shown in FIG. 1, although in other embodiments the first and second rods are substantially similar in length. In some embodiments, rod length is selected to allow a desired degree of growth of the spine 12. The rods 24, 26 each optionally include an enlarged stop feature 30, 32 having a larger diameter than adjacent portions of the respective rods 24, 26. In some embodiments, the stop features 30, 32 of the rods 24, 26 are thicker, shorter portions (e.g., with smooth rounded outline) which are hosted by wider areas of the connectors 18, 20 and are allowed to slide within the respective connectors 18, 20 until they abut narrower parts of the connectors. Each of the rods 24, 26 also includes thinner longer portions 36, 38.

As shown schematically in FIG. 1, the spine 12 generally includes five portions, where a defective segment of the spine 12 includes a proximal, or upper portion 40; a distal, or lower portion 42; and an apical portion, or apex 44. Above and below the defective segment 40, 42, 44, the spine 12 has a first portion 46 including one or more stabilizing vertebrae (e.g., a first vertebra 46A) and a second portion 48 including one or more stabilizing vertebrae (e.g., a second vertebra 48A). In some embodiments, the stabilizing vertebrae are substantially aligned and are optionally fused during, prior to, or after assembly of the system 10. In turn, the apical portion 44 includes one or more vertebrae at the apex of the defect (e.g., a third vertebra 44A, a fourth vertebra 44B, and a fifth vertebra 44C).

The thinner portions 36, 38 of the rods 24, 26 are adapted to host means of spinal fixation 34, 35, such as pedicle screws or hooks, to the first and second portions 46, 48 of spine 12 at both ends of the defective segment 40, 42, 44. For example, in some embodiments, the means of spinal fixation 34, 35 include pedicle screws or hooks used to secure the thinner longer portions 36, 38 of the rods 24, 26 to one or more vertebrae in each of the first and second portions 46, 48, respectively, of the spine 12. If desired, each of the thinner longer portions 36, 38 is secured to the first and second vertebrae 46A, 48A, respectively, of the first and second portions 46, 48. In some embodiments, one or both of the thinner longer portions 36, 38 are secured to multiple vertebrae, such as two adjacent stabilizing vertebrae of the first and second portions 46, 48, respectively (e.g., to provide additional support to the system 10).

In some embodiments, the middle assembling segment 22 includes a body portion 22A, such as a rod, a plate, or other structure for spanning between the first and second connectors 18, 20 and to which a vertebra (e.g., a third vertebra 44A in the apical portion 44) can be tensioned. The middle assembling segment 22 also optionally includes an interconnect portion 22B, such as a collar or a head of a pedicle screw, for connecting to the body portion 22A.

In some embodiments, the intermediate connector assembly 28 includes one or more elongate members, such as first elongate member 28A, second elongate member 28B, and third elongate member 28C. The elongate members 28A, 28B, 28C optionally include one or more cables, wires, pedicle screws, hooks, rods, and/or other means for spanning between the interconnect portion 22B of the middle assembling segment 22 and the apical portion 44. The elongate members 28A, 28B, 28C are optionally connected to the third, fourth, and fifth vertebrae 44A, 44B, 44C of the apical portion 44, respectively, by fastening means 49, such as threaded fasteners, adhesives, hooks, sublaminar wires, and/or others.

The first and second connectors 18, 20 optionally differ in length as shown in FIG. 1, although in other embodiments the connectors 18, 20 are substantially similar in length. The first and second connectors 18, 20 are adapted to extend along a desired spinal segment (e.g., including the upper and lower portions 40, 42). In some embodiments, the lengths of the first and second connectors 18, 20 are selected to allow a desired amount of longitudinal growth of the spine 12, where the connectors 18, 20 are each optionally cylindrical, having inner bores 50, 52 that have narrowed, neck portions 54, 56 and wider portions 58, 60 such that the inner bores 50, 52 include two parts with different diameters.

In some embodiments, the diameters of the wider portions 58, 60 of the bores 50, 52 are larger than the diameters of the thicker, stop features 30, 32 of the rods 24, 26 to allow introduction of the rods 24, 26 into the bores 50, 52, starting with the thinner portions 36, 38 of the rods 24, 26 which are first introduced through the openings into which the body portion 22A of the middle assembling segment 22 is subsequently inserted and secured. The stop features 30, 32 of the rods 24, 26 help retain the rods 24, 26 in the inner bores 50, 52 by engaging the narrowed or necked portions 54, 56 of the connectors 18, 20 and help prevent inadvertent ejection of the rods 24, 26 from the connectors 18, 20.

In some embodiments, each of the connectors 18, 20 includes two means of fixation (e.g., set screws, pins, or others) for selectively locking a longitudinal position of the rods 24, 26 with respect to the first and second connectors 18, 20, respectively. As used herein, "selectively locking" indicates that the longitudinal position is locked and unlocked as desired using the means of fixation of the first and second connectors 18, 20. According to some embodiments, independent control of each of the upper and lower portions 40, 42 of the deformity is achieved by preselecting a desired amount that each of the first and second rods 24, 26 is allowed to travel in the respective first and second connectors 18, 20 (e.g., by selecting a length of the connectors 18, 20 and rods 24, 26) and/or by selectively locking the rods 24, 26 using the means of fixation once a desired amount of growth is achieved.

Figure 4:
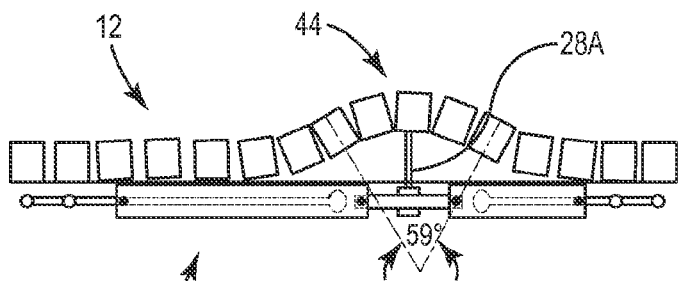
FIG. 4 shows the spine of FIG. 3 after application of the system of FIG. 1, according to some embodiments.
Figure 5:
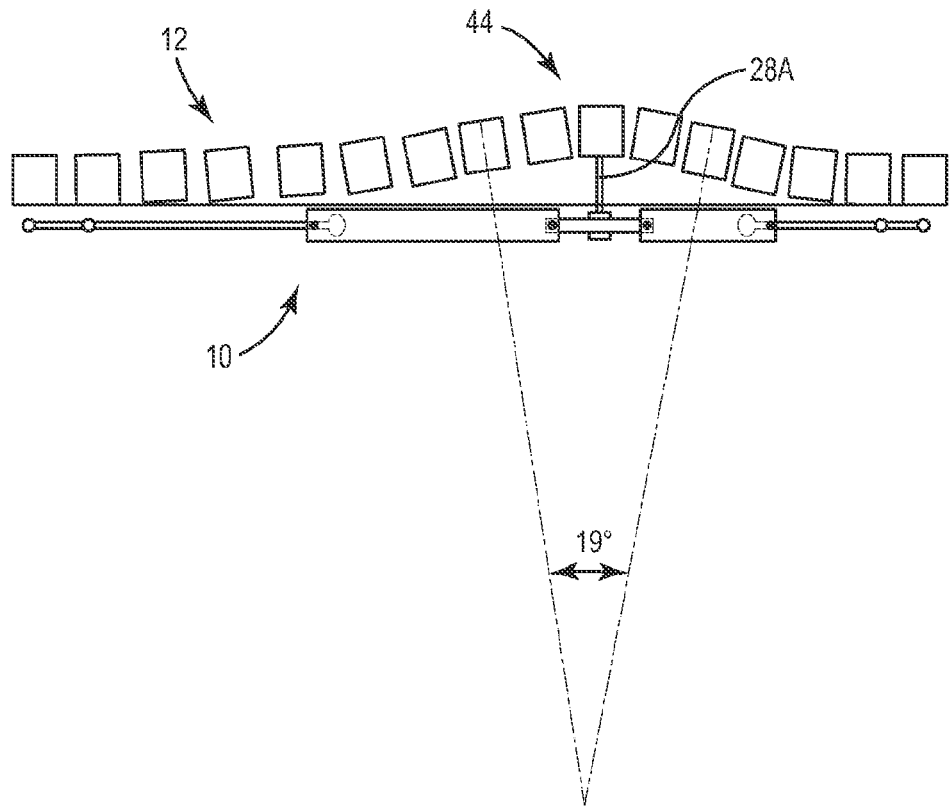
FIG. 5 shows the spine and system of FIG. 4 following spinal growth and elongation of the system, according to some embodiments.

FIG. 2 shows a first means of fixation 70 and a second means of fixation 72 of the first connector 18, where according to some embodiments the second connector 20 includes similar means of fixation that operate similarly to the first and second means of fixation 70, 72 (see FIGS. 4 and 5). In the embodiment shown in FIG. 2, the first and second means of fixation 70, 72 are located at each end of the connector 18. The second means of fixation 72 (e.g., a set screw) is optionally used to fix the connector 18 to the middle assembling segment 22, the middle assembling segment 22 being received in the central bore 50 of the connector 18. The first means of fixation 70 is a temporary fixation point to fix the connector 18 to the thinner portion 36 of the rod 24 as desired. The means for fixation of the second connector 20 optionally operate similarly and, by fixing the rods 24, 26 to the connectors 18, 20, the rods 24, 26, and connectors 18, 20 can be handled as one piece for ease of use during their insertion in the index surgery. Following insertion, the first means of fixation 70 of the first connector 18 and the first means of fixation (not shown) of the second connector 20 are released (e.g., unscrewed and/or removed) at the end of the procedure to disengage the connectors 18, 20 from the rods 24, 26 to allow for gradual sliding of the rods 24, 26 within the connectors 18, 20 with growth of the spine 12.

The diameters of the narrower, or thinner portions 36, 38 of the rods 24, 26 allow the thinner portions 36, 38 of the rods 24, 26 to go through the bores 50, 52, while the thicker stop features 30, 32 prevent the rods 24, 26 from ejecting from the bores 50, 52 and limit sliding of the rods 24, 26 to a desired range. In other words, the rods 24, 26 will slide in the connectors 18, 20 with the thicker parts of the rods 24, 26 moving out into the wider parts 58, 60 of the bores 50, 52 of the connectors 18, 20 until they abut against the narrower, necked portions 54, 56 of the bores 50, 52, preventing the rods 24, 26 from further sliding. At this point, the length of the rods 24, 26 and more generally the system 10 will be exhausted and the system 10 will likely need to be adjusted by exchanging the rods 24, 26 and/or connectors 18, 20 to longer sizes.

In some embodiments, the body portion 22A of the middle assembling segment 22 is introduced into, and fixed to both wider ends of the bores 50, 52 of the connectors 18, 20. Upon assembly and fixation to the first and second vertebrae 46A, 48A, the rods 24, 26, connectors 18, 20, and middle assembling segment 22 define a correction axis X extending between the first and second vertebrae 46A, 48A. The body portion 22A of the middle assembling segment 22 is assembled to the interconnect portion 22B which hosts the intermediate connector assembly 28. As described above, the intermediate connector assembly 28 optionally includes elongate members 28A, 28B, 28C that include one or more of cables, wires, pedicle screws, hooks, or other means for spanning between the middle assembling segment 22 and the intermediate connector assembly 28. The distance between the middle assembling segment 22 and the apical portion 44 can be decreased by shortening the length of this fixation tool to tension or draw the apical portion 44 (e.g., the third vertebra 44A) toward the correction axis X.

Some methods of assembly includes coupling the first and second rods 24, 26 with the first and second connectors 18, 20, and then coupling the first and second connectors 18, 20 together with the middle assembling segment 22. When assembled, the thinner portions 36, 38 of both rods 24, 26 extend out of the narrower openings or necked portions 54, 56 of the corresponding connectors 18, 20. The thinner portions 36, 38 may then be attached to the spine 12 proximal and distal to the spinal deformity via vertebral fixation implants (e.g., hooks, screws, or others) at the first and second vertebrae 46A, 48A. The bigger end of both rods 24, 26 (stop features 30, 32) will each be hosted inside the respective bores 50, 52 of one of the connectors 18, 20 near the wider portions 58, 60 of the bores 50, 52 and beside the middle assembling segment 22 to allow the rods 24, 26 to slide inside the bores 50, 52 during growth of the spine 12. Both wider portions 58, 60 of the bores 50, 52 of the connectors 18, 20 receive the body portion 22A of the middle assembling segment 22 which is then secured within the body portion 22A. The elongate member(s) 28A, 28B, 28C of the intermediate connector 28 are secured to the interconnect portion 22B of the middle assembling segment 22 and the elongate member(s) 28A, 28B, 28C are secured to the third, fourth, and fifth vertebrae 44A, 44B, 44C using the fastening means 49 to thereby fix and control the apical portion 44 with respect to the middle assembling segment 22.

Some methods of growth directed correction of the curvature with the system 10 proceeds as follows. The system 10 is applied and secured to the first portion 46 (e.g., first vertebra 46A), the second portion 48 (e.g., second vertebra 48A), and apical portion 44 (e.g., one or more of the third, fourth, and fifth vertebrae 44A, 44B, 44C), for example, after maximum correction has been achieved by surgery. Then, with growth, both bulkier ends or stop features 30, 32 of the rods 24, 26 will slide outwardly, away from the body portion 22A within the first and second connectors 18, 20 allowing for directed growth of the spine until the rods 24, 26 are exhausted and the bulkier parts, or stop features 30, 32 abut against the necked portions 54, 56 of the connectors 18, 20 and/or until the rods 24, 26 are locked at a desired position via the fixation means (e.g., set screws) of the first and second connectors 18, 20. This interaction allows for spontaneous growth (e.g., several centimeters) and many years of growth while keeping the distance between the middle assembling segment 22 and the apical portion 44. In some embodiments, the distance between the middle assembling segment 22 and the apical portion 44 is reduced using a specific instrument, such as a cable or wire tensioner (not shown).

Figure 3:
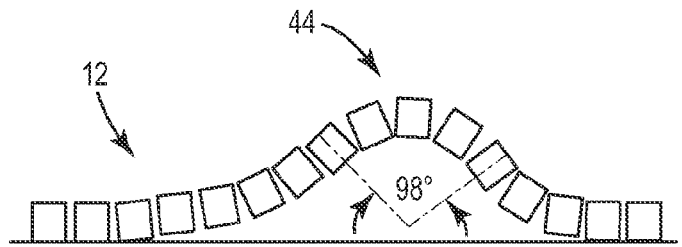
FIG. 3 is a schematic view of a scoliotic spine before correction with the system of FIG. 1, according to some embodiments.

A schematic representation of a method of growth directed correction is provided in FIGS. 3-5, where FIG. 3 shows the spine 12 having a scoliotic curve (e.g., a severe curve greater than about 90 degrees) prior to application of the system 10. FIG. 4 shows the spine 12 and the system 10 after application of the system 10. As shown in FIG. 4, and according to some embodiments, the system 10 is secured to the spine 12 with some amount of apical correction during fixation (e.g., to a curve of about 59 degrees). In some embodiments, partial correction is accomplished by drawing the apical portion 44 toward the system 10 as part of the apical fixation process. FIG. 5 shows the system 10 and spine 12 following spinal growth (e.g., a few years later) where the spine 12 and the system 10 have elongated causing growth directed correction of the spine 12 resulting gradually and spontaneously without further intervention (e.g., to a curve of about 19 degrees). In some embodiments, however, further intervention following some growth is contemplated to encourage and/or augment correction. For example, such intervention optionally includes reducing the distance between the system 10 and the apical portion 44 by tensioning and/or shortening one or more of associated elongate member(s) 28 (a single elongate member 28A is shown in FIGS. 4 and 5).

Various features and advantages of embodiments of the system 10 should be apparent from the foregoing. For example, in some embodiments, the system 10 is easy to fabricate, is low profile such that it is suitable for all ages, and efficient and effective in use. The system 10 is optionally assembled as a single construct via the temporary means of fixation between the rods 24, 26 and connectors 18, 20, promoting ease of insertion and securement to the spine. Once implanted, the system 10 is optionally designed to work over the course of multiple years without substantial intervention.

In view of the foregoing, various embodiments provide a vertebral system 10 for correction and controlled growth of the spine 12 compromising rod(s) 24, 26, a hosting connector assembly 16, and an intermediate connector assembly 28. Embodiments include rods 24, 26 with different diameters of its both ends, where the bigger ends of the rods 24, 26 are optionally smooth to allow sliding in first and second connectors 18, 20 having end openings of different diameters. The connectors 18, 20 optionally have a wider openings to allow introduction of the rods 24, 26 starting with their thinner then thicker parts inside the connectors 18, 20. The wider opening can accommodate and be fixed to a middle assembling segment 22 of the system 10 via any stable means of fixation (e.g., set screws, threads, or others). In some embodiments, the system 10 includes a middle assembling segment 22 that includes a rod or plate which is attached to the intermediate connector assembly 28, which is in turn secured to the apical portion 44 via vertebral fixation means (e.g., hooks, screws, wires, or other fastening means). The connectors 18, 20 provide temporary fixation (e.g., using set screws, pins, or others) to the rods 24, 26 during assembly and insertion of the system 10. The system 10 is optionally to correct spinal deformities by allowing for growth of the spine 12 and promoting further gradual correction of the deformity with growth.

In some embodiments, the system 10 is used for acute and gradual correction of spinal deformity which allows for spinal growth of the instrumented segment by elongating automatically with growth without the need for any intervention after insertion and connection to the spine 12. The system 10 includes a hosting connector assembly or assemblies 16, special rod(s) 24, 26 and intermediate connector(s) 28. The rods 24, 26 are allowed to slide inside the hosting connector assembly 16, in turn allowing for elongation of the whole system 10 and hence the instrumented part of the spine 12. A middle assembling segment 22 is fixed to the apex 44 of the deformity using an intermediate connector assembly 28 including one or more elongate members 28A, 28B, 28C secured to the apex 44 using fastener means (e.g., pedicle screws, hooks, wires, cables, adhesives, and/or other means) to help prevent progressive rotation, angulation, or other deformity progression.

The distance between the two ends of the system 10 are able to independently increase with time and growth, while the distance between the apex 44 of the deformity and the system 10 is fixed or can be shortened by mean of continuous tension of the apical fixation (e.g., by tensioning the elongate member(s) 28A, 28B, 28C) thereby allowing for gradual spinal deformity curve correction with growth. For example, in some embodiments, first and second connector(s) 18, 20 each have a cavity made of two parts with different diameters and lengths—a longer wider part and shorter narrower one. The connector(s) 18, 20 each have one opening at each end, each opening has a different diameter which corresponds to its adjacent cavity. In some embodiments, each rod 24, 26 has a thicker (bigger diameter) shorter part at the end of the rod 24, 26 with the aim of preventing the rod 24, 26 from dislodging from the smaller end opening of the corresponding connector 18, 20 when the system 10 reaches its maximal length. Each wider cavity of the connector(s) 18, 20 can host and allow the passage of both parts of the rod(s) 24, 26 while the narrower cavity of the connector(s) 18, 20 can host only the thinner part of the rod(s) 24, 26, thereby preventing the thicker end of the rod(s) 24, 26 from passing through the corresponding end opening of the connector(s) 18, 20.

In some embodiments, the middle assembling segment 22 connects the two hosting connectors 18, 20 together by being inserted into and secured within the wider openings and cavities of the connectors 18, 20. The rod(s) 24, 26 are introduced—their thinner parts first—into the wider openings of the connectors 18, 20 and are fixed temporarily therein. The body portion 22A of the middle assembling segment 22 is then inserted into the wider ends and fixed therein to interconnect the two connectors 18, 20 together. In some embodiments, the body portion 22A of the middle assembling segment 22 is a rod shaped, or contoured to conform with a desired shape of the spine 12 in order to promote a proper sagittal contour of the spine 12 and decrease an incidence of implant failure, for example. The middle assembling segment 22 is secured to the apical portion 44 by the intermediate connector 28, which includes fastening means such as pedicle screws, hooks, wires, cables, and/or other fastening means for fastening to the vertebrae at the apex 44 of the deformity. The connector(s) 18, 20 have means of fixation (e.g., set screw, pins, and/or others) proximate each end—at the wider end to fix the connectors 18, 20 to the middle assembling segment 22 and at the narrower end to fix the thinner part of the rods 24, 26 temporarily during assembly and insertion and attachment of the system 10 to the spine 12. In some embodiments, the temporary means of fixation, or selective locking means, are removed at the end of the procedure to allow one or both of the rods 24, 26 to slide in the connectors 18, 20 and to allow the system 10 to elongate.

As referenced above, the system 10 optionally facilitates independent, separate control of each of the upper and lower portions 40, 42 of a deformity, those upper and lower portions 40, 42 being situated proximal and distal to an apical portion 44 of the deformity. For example, a distance between each end of the system 10 and the apical portion 44 increases independently with time and growth of the spine 12, while the distance between the apical portion 44 and the system 10 is generally fixed or selectively adjusted (e.g., by tensioning the apical portion 44 toward the hosting connector assembly 16) allowing for gradual or gross spinal deformity curve correction. The first and second connectors 18, 20 optionally have different lengths, (e.g., to facilitate differing, independent, and preplanned control of the permissible growth and correction of the upper and lower portions 40, 42 of the spine 12). In some methods of differing, independent, and preplanned control, a deformity angle and number of vertebrae included in each of the upper and lower portions 40, 42 are taken into consideration in determining an appropriate amount of travel between the first rod 24 and the first connector 18 and between the second rod 26 and the second connector 20, where each of the first and second rods 24, 26 is able to slide independently of the other rod inside its corresponding connector to facilitate independent elongation of the system 10 along the instrumented portions of the spine 12 above and below the apical portion 44. In some methods of correction, the second mean of fixation of each of the first and second connectors 18, 20 can, at any time after the application of the system 10, be tightened to limit further elongation of the corresponding upper or lower portion 40, 42 of the spine 12. By including means for selectively limiting growth of the upper or lower portions 40, 42 of the spine 12, the system 10 is further adapted to promote independent correction of each of the upper and lower portions 40, 42 as desired.

Various modifications and additions can be made to the exemplary embodiments discussed without departing from the scope of the present invention. For example, a second system (not shown) substantially similar to the system 10 is optionally secured on an opposite side of the spine 12 for additional control. Moreover, while the system 10 is shown secured on a concave lateral aspect of the spine 12, it should be understood that, in some embodiments, the system 10 is secured on a convex lateral aspect of the spine 12.

Figure 6:
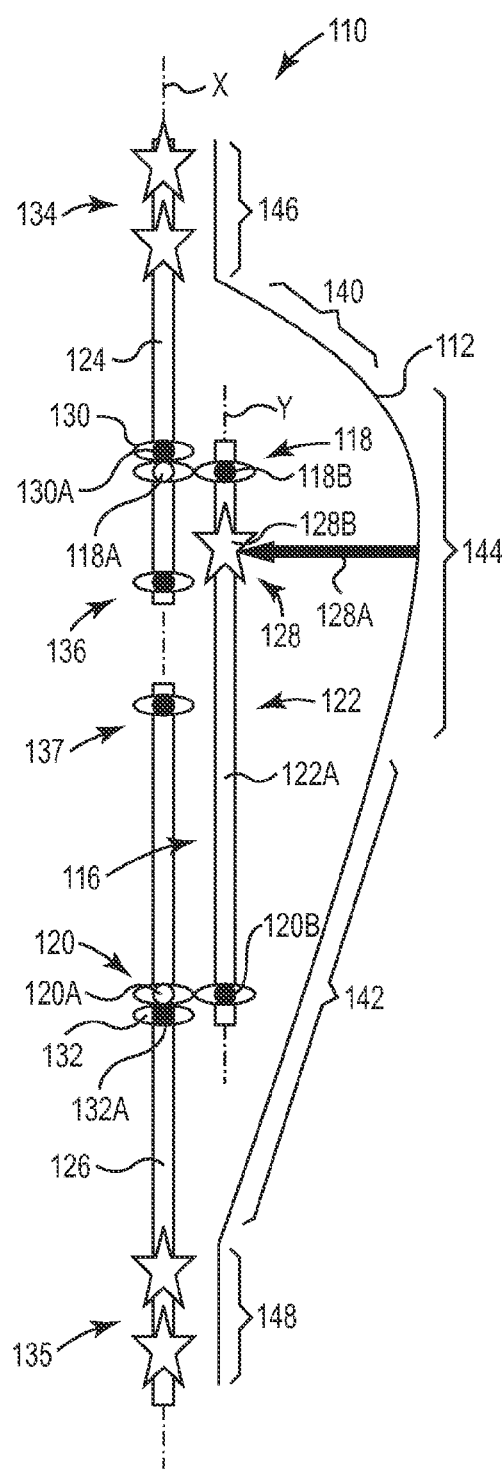
FIG. 6 is a schematic view of another corrective system secured along a spine tending to exhibit a defective curvature with a concave aspect, according to some embodiments.

FIG. 6 shows another system 110 for growth directed correction of a spine 112 (schematically represented by a single line) via control of one or more apical vertebrae. As shown, the system 110 includes a cascaded, or laterally offset feature, as subsequently described. As indicated schematically in FIG. 6, in some embodiments the system 110 is secured to the spine 112 along a concave aspect of its defective curvature. In some embodiments, the system 110 includes a hosting connector assembly 116 including a first connector 118, a second connector 120, and a middle assembling segment 122. In the various embodiments, the system 110 further includes a first rod 124, a second rod 126, and an intermediate connector 128.

The first and second rods 124, 126 are adapted to extend along the spine 112 and optionally differ in length as shown in FIG. 6, although in other embodiments the first and second rods 124, 126 are substantially similar in length. Regardless, in some embodiments, rod length is selected to allow a desired degree of growth of the spine 112.

As indicated, the spine 112 generally includes five portions, where a defective segment of the spine 112 includes a proximal, or upper portion 140; a distal, or lower portion 142; and an apical portion, or apex 144. Above and below the defective segment 140, 142, 144, the spine 112 has a first portion 146 including one or more stabilizing vertebrae and a second portion 148 including one or more stabilizing vertebrae. In some embodiments, the stabilizing vertebrae are substantially aligned and are optionally fused during, prior to, or after assembly of the system 110. In turn, the apical portion 144 includes one or more vertebrae at the apex of the defect.

In some embodiments, the rods 124, 126 are adapted to host means of spinal fixation 134, 135 for securing the first and second portions 146, 148 of spine 112 at both ends of the defective segment 140, 142, 144. In some embodiments, the means of spinal fixation 134, 135 include pedicle screws, hooks, adhesive, or other fastening means used to secure the rods 124, 126 to one or more vertebrae in each of the first and second portions 146, 148.

In some embodiments, the middle assembling segment 122 includes a body portion 122A, such as a rod, a plate, or other structure for spanning between the first and second connectors 118, 120 and to which one or more vertebrae in the apical portion 144 is tensioned. The middle assembling segment 122 also optionally includes an interconnect portion 122B, such as a collar or a head of a pedicle screw or hook, for connecting to the body portion 122A.

In some embodiments, the intermediate connector 128 includes one or more elongate members, such as a first elongate member 128A. The elongate member(s) optionally include one or more cables, wires, pedicle screws, rods, and/or other means for spanning between the middle assembling segment 122 and the apical portion 144.

In some embodiments, the first and second connectors 118, 120 are substantially shorter than the connectors 18, 20 of the system 10. For example, the first and second connectors 118, 120 are optionally about 10 mm in length (i.e., a direction substantially parallel to the longitudinal axes of the respective rods 124, 126) or less. The first connector 118 is adapted to slidably receive the first rod 124 and the middle assembling segment 122. The second connector 120 is adapted to slidably receive the second rod 126 and the middle assembling segment 122. The connectors 118, 120 are optionally substantially similar and thus are described with reference to the first connector 118, where FIGS. 8 and 9 are top and front views, respectively, of the first connector 118.

Figure 8:
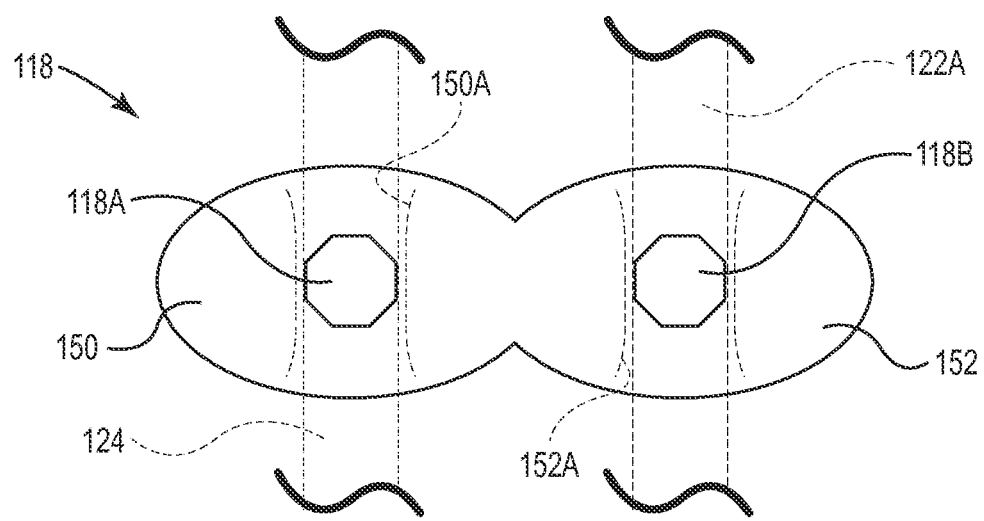
FIG. 8 is a top view of a dual-ring connector of the systems of FIGS. 6 and 7, according to some embodiments.
Figure 9:
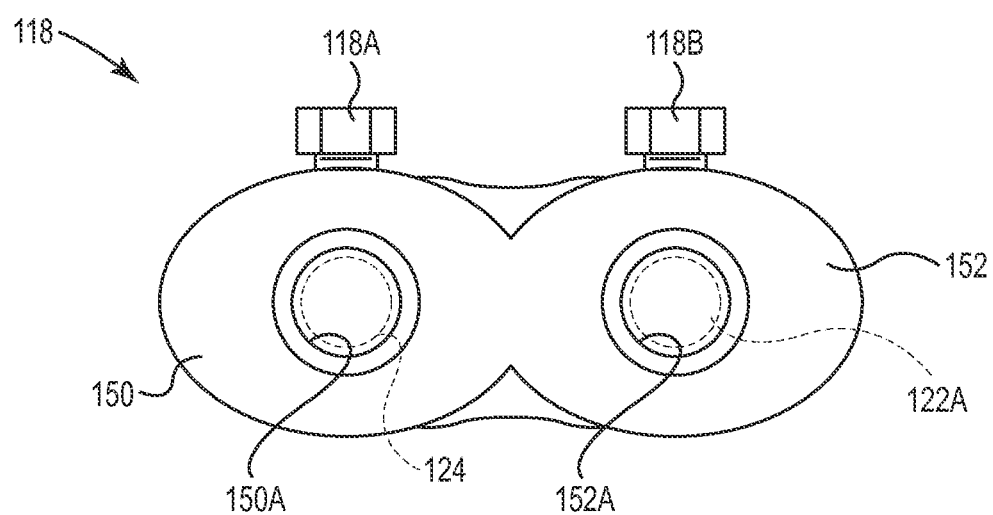
FIG. 9 is a front view of the dual-ring connector of FIG. 8, according to some embodiments.

As shown in FIGS. 8 and 9, the first connector 118 has a dual-ring shape, having a first ring portion 150 and a second ring portion 152, the second ring portion 152 being interconnected with the first ring portion 150. The first and second ring portions 150, 152 are optionally alternatively secured together by a rod or other connector. Indeed, although the two portions 150, 152 are shown as a single piece, in other embodiments the two portions 150, 152 are separate, connected components.

The ring portions 150, 152 include central bores 150A, 152A for receiving the first rod 124 and the middle assembling segment 122, respectively. As shown, the central bores 150A, 152A have entries and exits that are rounded to facilitate rod sliding and/or to avoid binding, for example. As shown, the central bores 150A, 152A are substantially circular and smooth. In other embodiments, the central bores 150A, 152A include a prominence, or chase feature (such as chase feature 138 shown in FIGS. 12 and 13) for inhibiting longitudinal rotation of the rod 124 and/or the body portion 122A in the central bores 150A, 152A. For example, in some embodiments, the rod 124 and/or body portion 122A include a complementary chase feature (such as chase 139 shown in FIG. 14) to the prominence so that the rod 124 and/or body portion 122A and the bores 150A, 152A interlock, stopping longitudinal rotation of the rod 124 and/or body portion 122A. In other embodiments, the rod 124 and body portion 122A and the bores 150A, 152A have complementary, non-circular cross-sections (square, octagonal, or D-shaped, for example) that mate to inhibit rotation of the rod 124 and body portion 122A in the bores 150A, 152A, respectively.

As shown in FIG. 6, each of the connectors 118, 120 includes two means of fixation (e.g., set screws, pins, or others) 118A, 118B and 120A, 120B, respectively, for selectively locking a longitudinal position of the connectors 118, 120 relative to the rods 124, 126 and the middle assembling segment 122. As shown in FIGS. 8 and 9, the means of fixation 118A, 118B are set screws secured into the two portions 150, 152, respectively, such that adjustment of the first means of fixation 118A selectively locks the first rod 124 in the first ring portion 150 and adjustment of the second means of fixation 118B selectively locks the middle assembling segment 122 in the second ring portion 152. For reference, in the schematic views of FIGS. 6 and 7, an open hexagon is indicative that the means of fixation is in an unlocked configuration and a solid hexagon is indicative that the means of fixation is in a locked configuration.

In some embodiments, the system 110 includes stop features 130, 132 that help prevent the rods from sliding toward one another, which could otherwise lead to reduction in the length of the system 110 in the longitudinal direction and loss of correction of the scoliosis angle. For example, the stop features 130, 132 optionally help limit the rods 124, 126 to sliding in a single direction—the direction of growth—and help prevent sliding in an opposite direction that would otherwise reduce overall system length. In some embodiments, the stop features 130, 132 are rings, or collars, that include set screws 130A, 132A for securing the stop features 130, 132 longitudinally along the first and second rods 124, 126, respectively.

In some embodiments, the system 110 also includes stop features 136, 137 that help prevent inadvertent ejection of the rods 124, 126 from the connectors 118, 120. For example, the stop features 136, 137 help ensure that the system 110 does not inadvertently disassemble after sufficient growth is achieved to cause the connectors to reach the ends of the rods 124, 126 and/or under sufficient flexing of the spine 112.

Figure 10:
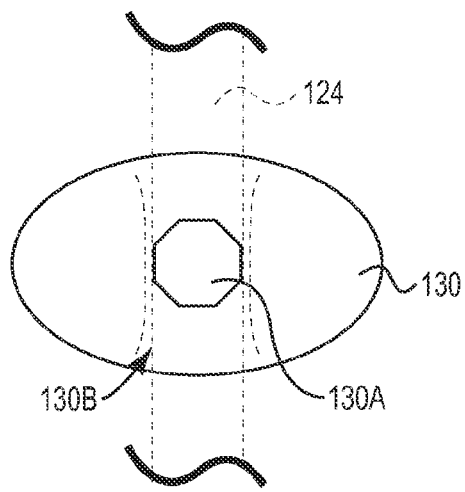
FIG. 10 is a top view of a single-ring connector of the systems of FIGS. 6 and 7, according to some embodiments.
Figure 11:
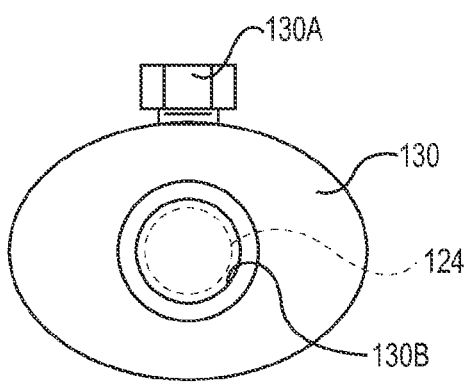
FIG. 11 is a front view of the single-ring connector of FIG. 10, according to some embodiments.

Generally, the stop features 130, 132, 136, 137 are substantially similar to the first and second connectors 118, 120, but rather than first and second ring portions, only a single ring portion is present, according to some embodiments. FIGS. 10 and 11 show the stop feature 130 from top and front views, respectively, the stop features 132, 136, 137 being substantially similar to the stop feature 130 according to some embodiments.

As shown in FIG. 6, each of the stop features 130, 132, 136, 137 includes a means of fixation (e.g., set screws, pins, or others) 130A, 132A, 136A, 137A, respectively, for selectively locking a longitudinal position of the stop features relative to the rods 124, 126. The means of fixation 130A, 132A, 136A, 137A are set screws secured into the stop features 130, 132, 136, 137, respectively. For example, as shown in FIGS. 10 and 11, adjustment of the means of fixation 130A selectively locks the first rod 124 in the stop feature 130. For reference, in the schematic views of FIGS. 6 and 7, an open hexagon is indicative that the means of fixation is in an unlocked configuration and a solid hexagon is indicative that the means of fixation is in a locked configuration.

As shown in FIGS. 10 and 11, the stop feature 130 has a single-ring shape, although multi-ring shapes are contemplated. The stop feature 130 includes a central bore 130B for receiving the first rod 124. As shown, the central bore 130B has an entry and an exit that are rounded to facilitate rod sliding and/or to avoid binding, for example. As shown, the central bore 130B is substantially circular and smooth, although non-rotational features are contemplated as described below.

Figure 12:
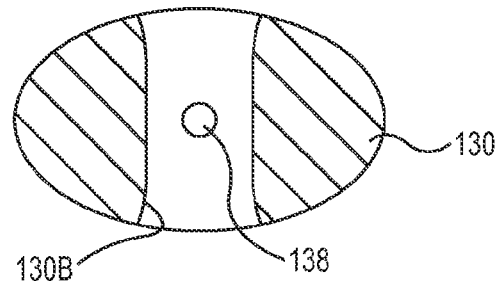
FIG. 12 is a top view of a lateral cross-section of another single-ring connector of the systems of FIGS. 6 and 7, according to some embodiments.
Figure 13:
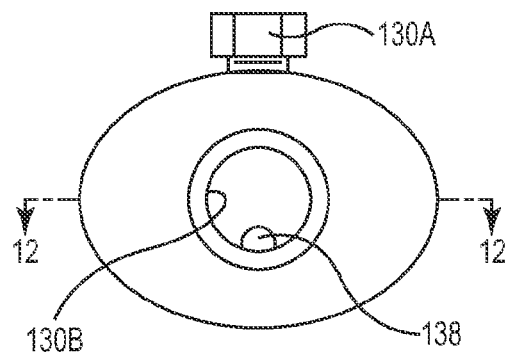
FIG. 13 is a front view of the single-ring connector of FIG. 12, according to some embodiments.
Figure 14:
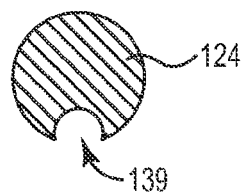
FIG. 14 shows a cross-section of a rod, according to some embodiments.

For example, FIGS. 12 and 13 show the stop feature 130 according to some other embodiments, where FIG. 12 is a cross-sectional view along line 12-12 in FIG. 13. As shown, the central bore 130B includes a prominence, or chase feature 138 for inhibiting longitudinal rotation of the rod 124 in the central bore 130B. The chase feature 138 is optionally a hemi-spherical bump or protrusion into the bore 130B. As shown in FIG. 14, in some embodiments, the rod 124 includes a chase feature 139, such as a longitudinal groove or chase, that is complementary to the chase feature 138 such that that the rod 124 and the bore 130B are adapted to interlock, helping prevent longitudinal rotation of the rod 124 in the bore 130B. In other embodiments, the rod 124 and the bore 130B have complementary, non-circular cross-sections (square, octagonal, or D-shaped, for example) that mate to inhibit rotation of the rod 124 in the bore 130B. Although the chase features 138, 139 are shown on the stop feature 130 and rod 124, respectively, it should be understood that the chase features 138, 139 are optionally reversed, with the chase feature 139 on the stop feature 130 and the chase feature 138 on the rod 124.

Regardless, according to some embodiments, independent control of each of the upper and lower portions 140, 142 of the deformity is achieved by preselecting a desired amount that each of the first and second rods 124, 126 is allowed to travel in the respective first and second connectors 118, 120. In some embodiments, the amount of travel is determined by selectively locking the stop features 130, 132, 136, 137 longitudinally along the first and second rods 124, 126 at a desired position to set limits of travel for the first and second rods 124, 126, respectively.

Some methods of assembling the system 110 include coupling the first and second rods 124, 126 with the first and second connectors 118, 120, and then coupling the first and second connectors 118, 120 to the middle assembling segment 122. When assembled, the rods 124, 126 extend out of the corresponding connectors 118, 120, with respective portions of the rods 124, 126 being secured to the spine 112 proximal and distal to the spinal deformity via vertebral fixation implants (e.g., hooks, screws, or others) at the first and second portions 146, 148 of the spine 112. The first rod 124 and the second rod 126 are hosted, or received, inside the bores of the respective connectors 118, 120 and are allowed to slide inside the bores of the corresponding connectors 118, 120 during growth of the spine 112.

Adjacent bores of the connectors 118, 120 receive the middle assembling segment 122 and are selectively locked to the body portion 122A to provide system stability. In the configuration shown in FIG. 6, the middle assembling segment defines a second axis of correction Y that is laterally offset, toward the spine 112, relative to a first axis of correction X defined by the longitudinal axes of the rods 124, 126, the two rods 124, 126 being coaxially aligned to one another according to some embodiments. In some embodiments, this offset brings the middle assembling segment 122 closer to the spine 112 reducing the length needed for the intermediate connector 128. The intermediate connector 128 is then secured to the apex 144 using fastening means such as those previously described (e.g., similar to fastening means 49). The respective stop features 130, 132, 136, 137 are received over the first and second rods 124, 126 and are selectively locked thereto in order to help prevent the rods 124, 126 from sliding toward one another (e.g., to avoid losing an amount of correction already achieved with the system 110) as well as help prevent the rods 124, 126 from sliding out of the connectors 118, 120 (e.g., after sufficient spinal growth and/or during flexing of the spine 112). In some embodiments, an additional set of stop features (not shown) are secured inwardly along the rods (e.g., toward the apical portion 144 of the spine 112) to set limits on the allowed longitudinal expansion of the system 110.

Some methods of growth directed correction of the curvature with the system 110 proceeds as follows. The system 110 is applied and secured to the first portion 146, the second portion 148, and the apical portion 144, for example, after maximum correction has been achieved via surgery. Then, with growth, both of the rods 124, 126 will slide outwardly, away from one another and adjacent to the body portion 122A. During growth, the rods 124, 126 will continue to slide within the first and second connectors 118, 120, allowing for growth-directed correction of the spine 112 until the rods 124, 126 are exhausted and/or until the rods 124, 126 are locked at a desired position via the fixation means of the first and second connectors 118, 120. This interaction allows for spontaneous growth and/or movement (e.g., several centimeters) and many years of growth while maintaining a constant distance between the middle assembling segment 122 and the apical portion 144. In some other embodiments, the distance between the middle assembling segment 122 and the apical portion 144 is periodically reduced during growth using a specific instrument, such as a cable or wire tensioner (not shown).

The system 110, and in particular the relatively short connectors, help facilitate placement of the system 110 in relatively compact areas of the spine 112 (e.g., in scoliotic curved regions which provide little area for longer, more bulky connectors). For example, a dorsal curve or an asymmetric curve regularly exhibits a relatively small distance between the stabilizing vertebrae and the apex in which a connector of about 50 mm in length may not fit. The dual-ring connector is deployable in a very short segment of the spine 112 while allowing for considerable length of rod bending and sliding and, thus, growth directed correction. Moreover, in some embodiments, the stop features 130, 132 are optionally used to direct the force in a single, expanding direction by preventing compression and shortening of the system 110 without interfering with elongation thereof.

Figure 7:
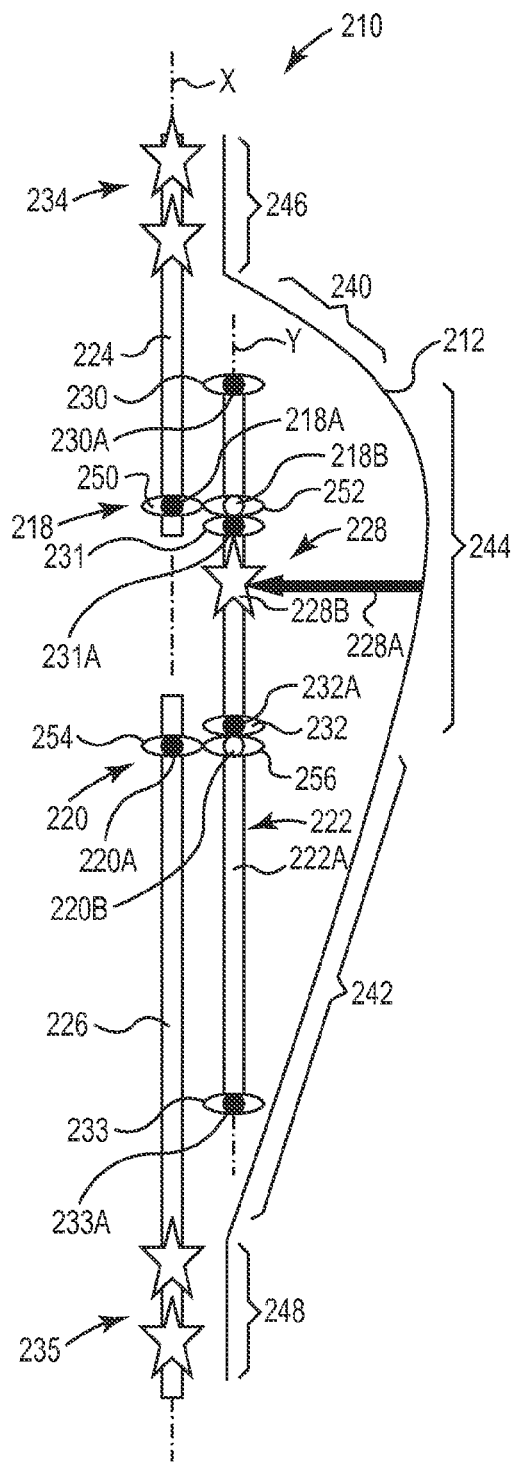
FIG. 7 is schematic view of another corrective system secured along a spine tending to exhibit a defective curvature with a concave aspect, according to some embodiments.

FIG. 7 is a schematic of another system 210 for growth directed correction of a spine 212 (schematically indicated by a single line) via control of one or more apical vertebrae. In some embodiments the system 210 is secured to the spine 212 along a concave aspect of its defective curvature. In some embodiments, the system 210 includes a hosting connector assembly 216 including a first connector 218, a second connector 220, and a middle assembling segment 222. In the various embodiments, the system 210 further includes a first rod 224, a second rod 226, and an intermediate connector 228.

The first and second rods 224, 226 are adapted to extend along the spine 212 and optionally differ in length as shown in FIG. 7, although in other embodiments the first and second rods 224, 226 are substantially similar in length. Regardless, in some embodiments, rod length is selected to allow a desired degree of growth of the spine 212.

As indicated, the spine 212 generally includes five portions, where a defective segment of the spine 212 includes a proximal, or upper portion 240; a distal, or lower portion 242; and an apical portion, or apex 244. Above and below the defective segment 240, 242, 244, the spine 212 has a first portion 246 including one or more stabilizing vertebrae and a second portion 248 including one or more stabilizing vertebrae. In some embodiments, the stabilizing vertebrae are substantially aligned and are optionally fused during, prior to, or after assembly of the system 210. In turn, the apical portion 244 includes one or more vertebrae at the apex of the defect.

In some embodiments, the rods 224, 226 are adapted to host means of spinal fixation 234, 235 for securing the first and second portions 246, 248 of spine 212 at both ends of the defective segments 240, 242. In some embodiments, the means of spinal fixation 234, 235 include pedicle screws or hooks used to secure the rods 224, 226 to one or more vertebrae in each of the first and second portions 246, 248.

In some embodiments, the middle assembling segment 222 includes a body portion 222A, such as a rod, a plate, or other structure for spanning between the first and second connectors 218, 220 and to which one or more vertebrae in the apical portion 244 is tensioned. The middle assembling segment 222 also optionally includes an interconnect portion 222B, such as a collar or a head of a pedicle screw or hook, for connecting to the body portion 222A.

In some embodiments, the intermediate connector 228 includes one or more elongate members, such as a first elongate member 228A. The elongate member(s) optionally include one or more cables, wires, pedicle screws, hooks, rods, and/or other means for spanning between the middle assembling segment 222 and the apical portion 244.

In some embodiments, the first and second connectors 218, 220 are substantially similar to the first connector 118 shown in FIGS. 8 and 9, the first and second connectors 218, 220 being substantially shorter than the connectors 18, 20 of the system 10. In particular, the first connector 218 is adapted to slidably receive the first rod 224 and the middle assembling segment 222 and the second connector 220 is adapted to slidably receive the second rod 226 and the middle assembling segment 222, each of the first and second connectors 218, 220 including first and second ring portions 250, 252 and 254, 256, respectively.

The ring portions 250, 252 include central bores for receiving the first rod 224 and the middle assembling segment 222, respectively, and the ring portions 254, 256 include central portions for receiving the second rod 226 and the middle assembling segment 222, respectively. As shown in FIG. 7, each of the connectors 218, 220 includes two means of fixation (e.g., set screws, pins, or others) 218A, 218B and 220A, 220B, respectively, for selectively locking a longitudinal position of the connectors 218, 220 relative to the rods 224, 226 and the middle assembling segment 222. The means of fixation 218A, 218B are optionally set screws secured into the ring portions 250, 252 and 254, 256, respectively. Activation of the first means of fixation 218A selectively locks the first rod 224 in the first ring portion 250 and activation of the second means of fixation 218B selectively locks the middle assembling segment 222 in the second ring portion 252. Activation of the first means of fixation 220A selectively locks the second rod 226 in the first ring portion 254 and activation of the second means of fixation 220B selectively locks the middle assembling segment 222 in the second ring portion 256. For reference, in the schematic views of FIGS. 6 and 7, an open hexagon is indicative that the means of fixation is in an unlocked configuration and a solid hexagon is indicative that the means of fixation is in a locked configuration.

In some embodiments, the system 210 includes stop features 230, 233 that help retain the middle assembling segment 222 in the first and second connector assemblies 218, 220 by preventing inadvertent ejection of the middle assembling segment 222 from the connectors 218, 220 (e.g., after sufficient spinal growth and/or during flexing of the spine 212). The system 210 also includes stop features 231, 232 that help ensure that an achieved amount of correction of the spine 212 is not lost (e.g., due to compressive forces on the patient's spine—such as during standing). In some embodiments, the stop features 230, 231, 232, 233 are rings, or collars, that include set screws 230A, 231A, 232A, 233A for securing the stop features 230, 231, 232, 233 longitudinally along the middle assembling segment 222. In some embodiments, stop features 231, 232 help prevent collapse, or shortening of the system (e.g., under compressive forces of body weight) while stop features 230, 233 help prevent ejection of the middle assembling segment 222 from the connector assemblies 218, 220 once a length of the middle assembling segment 222 has been exhausted from spinal growth.

Generally, the stop features 230, 231, 232, 233 are substantially similar to the first and second connectors 218, 220, but rather than first and second ring portions, only a single ring portion is present, according to some embodiments. Regardless, according to some embodiments, independent control of each of the upper and lower portions 240, 242 of the deformity is achieved by preselecting a desired amount that the system 210 expands, or an amount that each of the first and second rods 224, 226 is allowed to travel along the middle assembling segment 222, by selectively locking the stop features 230, 231, 232, 233 longitudinally at desired positions to set limits of travel for the first and second rods 224, 226, respectively. For example, as shown in FIG. 7, the stop features 230, 231 are locked on the middle assembling segment 222 on opposite sides of the first connector 218 and the stop features 232, 233 are locked on the middle assembling segment 222 on opposite sides of the second connector 220, to limit the travel of first and second connectors relative to the middle assembling segment 222.

Some methods of assembling the system 210 include coupling the first and second rods 224, 226 with the first and second connectors 218, 220, and then coupling the first and second connectors 218, 220 to the middle assembling segment 222. When assembled, the rods 224, 226 extend out of the corresponding connectors 218, 220, with respective portions of the rods 224, 226 being secured to the spine 212 proximal and distal to the spinal deformity via vertebral fixation implants (e.g., hooks, screws, or others) at the first and second portions 246, 248 of the spine 212. A first end 224A of the first rod 224 and a first end 226A of the second rod 226 are hosted inside the bores of the respective connectors 218, 220 and are selectively locked inside the bores of the corresponding connectors 218, 220 during growth of the spine 212.

Adjacent bores of the connectors 218, 220 slidably receive the middle assembling segment 222 (although the connectors 218, 220 are optionally locked to the middle assembling segment 222 during implantation to provide a rigid construct that is more readily handled, or to provide system stability). In the configuration shown in FIG. 7, the middle assembling segment 222 defines a second axis of correction Y that is laterally offset, toward the spine 212, relative to a first axis of correction X defined by the longitudinal axes of the rods 224, 226, the two rods 224, 226 being coaxially aligned to one another according to some embodiments. In some embodiments, this offset brings the middle assembling segment 222 closer to the spine 212 reducing the length needed for the intermediate connector 228. The intermediate connector 228 is then secured to the apex 244 using fastening means such as those previously described (e.g., similar to fastening means 49).

The respective stop features 230, 231, 232, 233 are received over the intermediate connector 228 and are selectively locked thereto in order to set limits between which the first and connectors 218, 220 slide on the middle assembling segment.

Some methods of growth directed correction of the curvature with the system 210 proceeds as follows. The system 210 is applied and secured to the first portion 246, the second portion 248, and the apical portion 244, for example, after maximum correction has been achieved via surgery. Then, with growth, both of the rods 224, 226 will slide outwardly, away from one another and adjacent to the body portion 222A. During growth, the rods 224, 226, and in particular the first and second connectors 218, 220, will continue to slide along the middle assembling segment 222, allowing for growth-directed correction of the spine 212 until the limit of travel is exhausted and/or until the rods 224, 226 are locked at a desired position via the fixation means of the first and second connectors 218, 220. This interaction allows for spontaneous growth and/or movement (e.g., several centimeters) and many years of growth while maintaining a constant distance between the middle assembling segment 222 and the apical portion 244. In some other embodiments, the distance between the middle assembling segment 222 and the apical portion 244 is periodically reduced during growth using a specific instrument, such as a cable or wire tensioner (not shown).

The system 210, and in particular the relatively short connectors, help facilitate placement of the system 210 in relatively compact areas of the spine 212 (e.g., in scoliotic curved regions which provide little area for longer, more bulky connectors). For example, a dorsal curve or an asymmetric curve regularly exhibits a relatively small distance between the stabilizing vertebrae and the apex in which a connector of about 50 mm in length may not fit. The dual-ring connector is deployable in a very short segment of the spine 212 while allowing for considerable length of rod bending and sliding and, thus, growth directed correction. Moreover, in some embodiments, the stop features 230, 232 are optionally used to direct the force in a single, expanding direction by preventing compression and shortening of the system 210 without interfering with elongation thereof.

Various features and advantages of embodiments of the systems 10, 110, 210 should be apparent from the foregoing. For example, in some embodiments, such systems are easy to fabricate, are low profile to be suitable for all ages, and efficient and effective in use. The systems are optionally assembled and implanted as a single construct via the various means of fixation, with subsequent unlocking of the system to permit the desired expansion, promoting both ease of insertion and ready securement to the spine. Once implanted, the systems are designed to work over the course of multiple years without substantial intervention.

The range of indication of embodiments of the systems is wide enough to include any type of early onset spinal deformity of any etiology from the very young ages to the adolescent growth spurt, for example. One exemplary indication is early onset scoliosis where the systems are used in young children to allow for growth of the spine, trunk, chest, and lungs while preventing progression of the scoliotic curve and even correcting the curve spontaneously with growth. The systems can also be used in small and moderate sized curves during the adolescent period before severe progression as a kind of internal bracing to help prevent further progression of these defective curves until a child's growth spurt finishes. In some embodiments, once the growth spurt has ended, the systems are removed, leaving a non-fused, relatively flexible, corrected spine.

While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention is claimed is:

1. A method for growth directed correction of a spine via apical vertebral control, the method comprising:

securing a correction system to a first vertebra and a second vertebra of the spine, the correction system having a first rod defining a first correction axis extending along the spine, a second rod coaxial with the first correction axis, and a connector assembly coupled to the first and second rods, the connector assembly including a middle assembling segment having a central longitudinal axis laterally offset from the first and second spinal rods, the central longitudinal axis defines a second correction axis extending along the spine, the connector assembly further including an intermediate connector extending from the second correction axis towards the spine in a direction transverse to first and second correction axes; and securing the intermediate connector of the connector assembly to a third vertebra that is intermediate the first and second vertebrae, the correction system securing the third vertebra at a fixed distance from the second correction axis;

wherein the correction system is secured to the first and second vertebrae such that the first and second vertebrae are able to grow away from one another in a direction substantially parallel to the second correction axis; and wherein the system allows growth of the first and second vertebrae away from one another within a predefined limit.

2. The method of claim 1, further comprising tensioning the third vertebra toward the second correction axis to a desired position and locking a lateral position of the third vertebra relative to the second correction axis.

3. The method of claim 1, wherein the spine tends to exhibits a defective curvature having a concave aspect having an apical vertebra, the first vertebra being located above the apical vertebra, the second vertebra being located below the apical vertebra, and the third vertebra being selected from a group consisting of the apical vertebra and a vertebra adjacent the apical vertebra.

4. The method of claim 1, wherein securing the correction system to the first vertebra and the second vertebra of the spine includes securing the first rod to the first vertebra and securing the second rod to the second vertebra.

5. The method of claim 1, wherein securing the correction system to the first vertebra and the second vertebra of the spine includes slidably securing the connector assembly to the first rod and securing the connector assembly to the second rod.

* * * * *